United States Patent [19]

Livache et al.

[11] Patent Number: 5,795,715
[45] Date of Patent: Aug. 18, 1998

[54] PROCESS FOR PREPARING DOUBLE-STRANDED RNA, AND ITS APPLICATIONS

[75] Inventors: Thierry Livache, Grenoble; Brigitte Fouque, Seyssinet; Robert Teoule, Grenoble, all of France

[73] Assignee: CIS Bio International, Saclay, France

[21] Appl. No.: 244,722

[22] PCT Filed: Dec. 18, 1992

[86] PCT No.: PCT/FR92/01209

§ 371 Date: Jun. 17, 1994

§ 102(e) Date: Jun. 17, 1994

[87] PCT Pub. No.: WO93/12229

PCT Pub. Date: Jun. 24, 1993

[30] Foreign Application Priority Data

Dec. 18, 1991 [FR] France ................... 91 15710

[51] Int. Cl.$^6$ .................. C12P 19/34; C12Q 1/68; C12N 15/00
[52] U.S. Cl. .................. 435/6; 435/91.1; 935/77; 935/78
[58] Field of Search .................. 435/6, 91.2, 91.1; 935/77, 78

[56] References Cited

U.S. PATENT DOCUMENTS 4,766,072  8/1988  Jendrisak et al. .................. 435/91

FOREIGN PATENT DOCUMENTS

WO90/14090  11/1990  WIPO.

OTHER PUBLICATIONS

Sadhu et al., Biochemistry International 14(6):1015–1022 (1987).

*Primary Examiner*—W. Gary Jones
*Assistant Examiner*—Ethan Whisenant
*Attorney, Agent, or Firm*—Oblon, Spivak, McClelland, Maier & Neustadt, P.C.

[57] ABSTRACT

A method for preparing double stranded RNA, wherein the simultaneous transcription of two complementary DNA sequence strands in a single reaction mixture is preformed, and the two resulting transcripts are immediately hybridized. The double stranded RNA fragments may be used for detecting and/or assaying nucleic acid target sequences in a biological sample.

11 Claims, 4 Drawing Sheets

1

PROCESS FOR PREPARING DOUBLE-STRANDED RNA, AND ITS APPLICATIONS

This application is a 371 filing of PCT/FR92/01209 filed 18 Dec. 1992.

FIELD OF THE INVENTION

The present invention relates to a process for the synthesis of double-stranded RNA, and to its applications.

DESCRIPTION OF THE BACKGROUND

Double-stranded ribonucleic acids are naturally rare and they are indeed present only in certain microorganisms such as yeasts or viruses. Up until recently, double-stranded RNA was only considered as a molecule of essentially theoretical interest, and whose possible applications were relevant only in basic research.

However, it has been demonstrated that double-stranded RNAs can, transiently, be involved in phenomena of regulation of expression, as well as in the initiation of the synthesis of interferon by cells [(DECLERQ et al., Methods in Enzymology, 1981, 78, 291 and WU-LI. J. Biol. Chem., 1990, 265, 5470)] and that they had anti-proliferative properties, which makes it possible also to envisage therapeutic applications (AUBEL et al., Proc. Natl. Acad. Sci., USA 1991, 88, 906).

It is therefore important to be able practically to synthesize double-stranded RNA (dsRNA) of determined sequence and length.

However, the production of double-stranded RNA is considered difficult. The few processes described up until now can be divided into three categories.

1) Extraction of double-stranded RNA from biological material

The extraction of double strands of RNA from viruses has been described, for example by BOCCARDO G. et al. (Double stranded RNA viruses, 1983, Bishop Eds. Elsevier, New York) and more recently by DULIEU et al. (J. Virol. Methods, 1989, 24, 77–84).

The presence of dsRNA in certain yeasts has been demonstrated by FRIED et al. (Proc. Natl. Acad. Sci. USA, 1978, 75, 4225) and by AL-HAKEEM et al. (Anal. Biochem., 1987, 163, 433–439).

While the extraction of dsRNA from yeasts is advantageous from the quantitative point of view, the sequences and lengths of the dsRNA are of course determined by the microorganism itself. It is a good route for production of dsRNA as raw material, but does not at all permit the synthesis of a predetermined sequence.

2) Hybridization of 2 single-stranded RNAs

The synthesis of dsRNA by hybridization of two complementary single-stranded RNAs has been described by SADHER et al., (Biochem. Int., 1987, 14, 1015). Each RNA chain is then synthesized by in vitro transcription of a recombinant plasmid containing, downstream of a promoter sequence of a DNA-dependent RNA polymerase, the DNA sequence to be transcribed. The single-stranded RNAs are then purified and quantified and then combined to form, by hybridization, a double strand of RNA.

More recently, BHATTACHARYYA (Nature, 1990, 343, 484) uses the RNA synthesis described by MILLIGAN (Nucleic Acids Res., 1987, 21, 8783) consisting in the transcription of a synthetic DNA template to RNA. The single-stranded RNAs are then combined and hybridized with each other.

2

These techniques are relatively long and difficult to implement because they necessitate the preparation of two recombinant or synthetic template DNAs and the purification of the two RNA strands produced prior to the hybridization.

3) Production of homopolymeric double-stranded RNA

J. YANO et al. (French Patent Application 2 617 403) describe a process for preparing double-stranded RNA of defined length, but of repetitive or homopolymeric sequence. In no case is this technique applicable to the synthesis of RNA of more complex sequence.

However, the inventors have now developed a process permitting the synthesis of double-stranded RNA from a DNA template of given sequence. They have indeed observed that if the simultaneous transcription of the two complementary strands of a DNA sequence is carried out under determined conditions and in the same reaction compartment, the two transcripts formed hybridize immediately between themselves, thus giving rise to a double-stranded RNA.

SUMMARY OF THE INVENTION

The subject of the present invention is a process for preparing double-stranded RNA, which process is characterized in that the simultaneous transcription is carried out of the two complementary strands of a DNA sequence which are present in the same reaction mixture. For this purpose, the sequence to be transcribed on each of the said DNA strands is placed under the control of a promoter sequence.

DETAILED DESCRIPTION OF THE PREFERRED EMBODIMENTS

Figure 1:
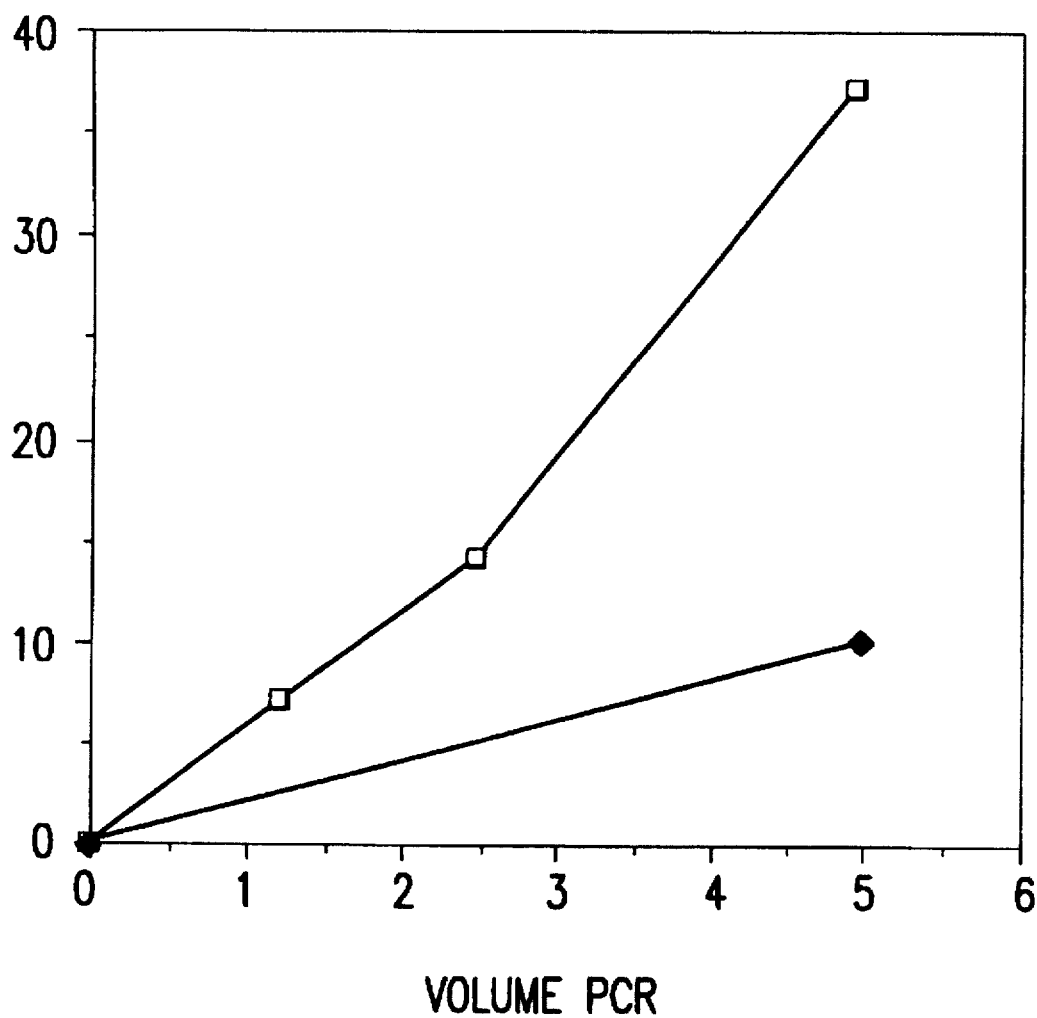
FIG. 1 is a graph depicting the fluorescence of DNA after PCR amplification as described in Example 1.

Promoter is understood to mean any double-stranded sequence of DNA comprising a binding site recognized by a DNA-dependent RNA polymerase. The binding of RNA polymerase to this promoter sequence permits initiation of transcription.

Among the promoter sequences which can be used within the framework of the present invention, there may be mentioned for example the sequences recognized by the RNA polymerases of phages T7, T3 or SP6. This does not however represent a limitation because it will appear clearly to a person skilled in the art that any promoter sequence identified as such, and for which the corresponding RNA polymerase is available, can a priori be used.

According to a preferred embodiment of the present invention, the two strands of DNA which are intended to be transcribed belong to two different duplexes which they each form with a DNA strand of at least partially complementary sequence.

According to another preferred embodiment of the present invention, the two strands of DNA intended to be transcribed are associated in the same duplex.

In this embodiment, the DNA sequence to be transcribed into double-stranded RNA is flanked by two promoters, one controlling the transcription of one of the strands, and the other that of the complementary strand. These two promoters may be identical or different.

The inventors have indeed observed that a DNA duplex provided at each end with a promoter sequence can directly generate RNAs of defined length and which can join in pairs to form a double-stranded RNA.

This is very surprising when the mode of action of RNA polymerases is considered; the enzyme binds to the promoter sequences and moves along the DNA template, synthesizing the complementary RNA strand. It was up until now assumed that if the DNA template contained two promoter sequences, the movement of the enzymes going in opposite directions was disrupted, resulting in sequences which are incomplete and therefore difficult if not impossible to pair.

However, the inventors have observed that, contrary to what was previously assumed, it is possible to transcribe simultaneously and completely the two complementary strands of a DNA duplex; the hybridization of the two complementary chains of RNA which are formed is thus immediate.

Under these conditions, the yield for the synthesis of double-stranded DNA is better than that for a single strand since the RNA formed in duplex form is more inert than single-stranded RNA with respect to the DNA template and nucleases.

Various methods for producing double strands of template DNA equipped with promoters can be used.

As example, there may be mentioned the following 3 methods

The template double strand can be constructed by direct hybridization of two oligonucleotides of complementary sequences, which are derived from chemical synthesis. Each oligonucleotide carries, at each end, the sequence of a promoter specific for an RNA polymerase, preferably that of an RNA polymerase derived from a phage, such as the RNA polymerase from the T7 phage (such sequences have been described, for example, by CHAMBERLIN, The enzymes, 1982, vol XV, Academic Press).

These two single-stranded DNAs are added in equimolar quantities and then hybridized with each other. A double strand of DNA is thus obtained which, in the case of synthetic oligonucleotides, can have a length preferably of between 40 and 100 base pairs, and which is equipped at each end with a promoter sequence.

The double strand of DNA can also be obtained by partial hybridization of two oligonucleotides on a short fragment of the 3' end, and then by extension of the 3' ends by a DNA polymerase. This technique makes it possible to obtain DNA templates which are of greater length and cheaper than those described earlier.

The third method consists of integrating primers carrying in 5' promoter sequences of at least one RNA polymerase in the DNA to be transcribed by an amplification process such as PCR (Polymerase Chain Reaction), LCR (Ligase Chain Reaction), NASBA (Nucleic Acid Sequence—Based Amplification) and the like (for review see RICHARD, Curr. Op. Biotec., 1991, 2, 76–85). A double-stranded DNA is thus obtained at the end of the reaction having a length preferably of between 50 and 1000 base pairs and provided at each end with a promoter sequence for an RNA polymerase.

The PCR process is described by SAIKI (Science, 1985, 230, 1350 and Science, 1988, 239, 487). The integration of a promoter by PCR is described by MURAKAWA (DNA, 1988, 7, 287) and in Patents WO 89/07149 (SOMMER) and WO 89/01050 (BURG), which describe the processes for the synthesis of single-stranded RNA.

For the implementation of the process conforming to the invention, the DNA templates thus obtained are incubated in the presence of the RNA polymerase (or the RNA polymerases) recognizing the promoter(s) carried by these templates, and ribonucleotide triphosphates. The reaction conditions are determined according to the type of RNA polymerase chosen.

It is particularly advantageous to use a low concentration of enzyme, between 10 and 50 units, and a high concentration of ribonucleotide triphosphates (between 1 and 5 mM).

For example, in the case of T7 phage RNA polymerase, 20 units of enzyme and 2.5 mM of each ribonucleotide triphosphate are preferably used.

Under these conditions, the two complementary chains of RNA which are formed hybridize instantly to form a double-stranded RNA which is more stable and more inert than a single-stranded RNA. Each template DNA generates at least a hundred or so RNA chains.

The double-stranded RNAs obtained from a template of DNA comprising a promoter on each strand exist as the copy in the form of RNA of the template DNA, whose 3' ends consist of a single strand of sequence which is complementary to that of the promoter.

All the DNA template duplexes can optionally be linked to a support; this attachment can for example be carried out by addition to the 5' end of at least one of the oligonucleotides, of a ligand such as biotin, which can be attached to a support coated with avidin. This attachment not only permits a more rapid purification of the double-stranded RNA synthesized, but also a possible reuse of the template attached to the support.

The double-stranded RNA thus obtained in conformity with the invention can be either separated from the DNA and optionally purified (this operation is simplified if the DNA template is attached to a support), or used or quantified directly if this technique is used as analytical tool.

The process conforming to the invention, by virtue of the fact that it is easy to implement, permits numerous applications.

It makes it possible indeed to obtain, in a single step, a large quantity of double-stranded RNA fragments of determined length and sequence, which the prior art processes did not permit.

The fragments thus obtained can of course be used in the various applications relating to basic research, or therapy, which are recommended in the prior art (Cf. for example the publications by DECLERQ, WU-LI and AUBEL; cited earlier).

In addition, the process for the synthesis of double-stranded RNAs conforming to the invention permits a completely new application which had never been suggested before, relating to the use of double-stranded RNA fragments for diagnosis, and in particular for the detection of target nucleic acid sequences in a biological sample. For the purposes of the present invention, target sequence denotes any nucleic acid sequence whose presence it is desired to detect in a sample to be analyzed.

A great number of diagnostic methods involve the detection of a specific sequence of nucleic acid in a biological sample.

The first processes of detection which were proposed involve probes consisting of single-stranded nucleic acid fragments complementary to the target sequence to be detected. These probes are, in addition, labelled, which permits the direct visualization of the target sequence/probe hybridization product.

However, this technique allows only the detection of sequences represented in a sufficiently large number of copies to permit the production of a visible hybridization signal.

It was therefore proposed, in order to improve the detection of a target sequence, to increase the number of copies thereof.

The techniques which are currently most frequently used for this purpose are based on the principle of the polymerase chain amplification, or PCR (Polymerase Chain Reaction). This technique permits the selective amplification of a double-stranded DNA sequence.

The principle of PCR, which is well known, will be only briefly recalled below: the amplification of a target sequence is performed by a series of cycles, each cycle comprising denaturation of the DNA comprising the sequence to be amplified;

annealing of primers flanking the said sequence at the 3' end of each of the strands to be amplified;

extension in 3' of the primers by a DNA polymerase;

denaturation of the DNA duplexes resulting from the extension of the primers, which initiates a new cycle.

The target sequence is thus, in theory, exponentially amplified; in practice, after the exponential amplification phase, a plateau phase is reached and about $10^5$ copies are obtained after 30 amplification cycles.

The double-stranded DNA fragments resulting from the amplification of the target sequence can then be identified, either by hybridization with a labeled specific probe, or by direct visualization after agarose gel electrophoresis in the presence of an intercalating agent such as ethidium bromide, and the like.

However, the PCR amplification techniques pose certain problems which complicate their use, in particular for the analysis of a large number of samples.

Detection techniques involving the hybridization of a labeled probe are generally considered as being highly specific since the probe is chosen so as to recognize only the target sequence. They have however the disadvantage of necessitating the use of labelled probes which are expensive, and whose hybridization necessitates several additional steps which increase the handling time.

Within the framework of serial analyses, it is much faster and less expensive to perform a direct visualization of the amplified fragments. However, this direct visualization involves an intercalating molecule which does not bind solely to the amplified fragments, but on all the nucleic acids present in the reaction mixture, which produces a high background.

The invention now provides a solution to this problem, by proposing the detection of copies in the form of double-stranded RNA, of the DNA fragments resulting from the amplification of the target sequence.

By virtue of the process conforming to the invention, these copies in the form of double-stranded RNA can be easily obtained.

It has already been proposed (for example by European Patent 397 269, and by Patent PCT 88/10315), in order to improve the detection of a target sequence, to synthesize single-stranded RNA, from a double-stranded DNA copy of this target sequence, in one of whose strands a promoter has been inserted, and optionally to amplify the single-stranded transcripts obtained, by the action of replicase QB.

However, the detection of the single-stranded RNAs thus obtained is achieved only by hybridization of specific probes, and on the other hand, the single-stranded RNAs are easily degraded by nucleases. In contrast, the double-stranded RNAs obtained in conformity with the invention do not present these disadvantages.

The use of the process for producing double-stranded RNA conforming to the invention for the detection of specific sequences in a biological sample advantageously supplements a PCR-type technique of which it makes it possible to increase the specificity and sensitivity.

For example, a template DNA provided with promoters can be specifically produced, from a nucleic acid sample, by a technique such as PCR, using primers containing promoter sequences for the amplification of the target sequence. Only a positive sample containing the target sequence will permit the synthesis of the DNA template. This template is then transcribed into at least a hundred or so copies of double-stranded RNA by (an) RNA polymerase(s). This double-stranded RNA, having a length and sequence which are defined by the template and therefore by the target nucleic acid, can then be quantified by appropriate means for assaying nucleic acids.

It should indeed be noted that the presence of a double-stranded RNA in the medium implies the presence of the target nucleic acid in the sample; indeed, if the sample is negative, the template DNA does not form and the promoters then remain in the form of single strands of DNA which cannot be recognized by RNA polymerase.

The detection or assay of the double-stranded RNA formed can be carried out by any appropriate means, such as hybridization with a nucleic acid probe specific for the sequence to be detected; it is particularly advantageous to carry out this detection in a homogeneous medium, by measurement of a signal induced by the specific interaction of an intercalating molecule with the double chain of RNA. This revealing does not necessitate the use of a specific probe, nor that of a support. It is therefore rapid and inexpensive.

Various intercalating agents can be used to detect the double-stranded RNA obtained by the process conforming to the invention. Those which interact more specifically with RNA than with DNA are preferred. The inventors have in particular observed that the use of the ethidium homodimer or of propionium iodide as intercalating agent made it possible to detect and assay the RNA obtained, under excellent conditions of sensitivity and specificity.

Compared with a direct measurement of the fluorescence in the presence of an intercalating agent of the quantity of DNA resulting from a PCR, the process conforming to the invention has the following advantages the transcription which generates at least a hundred or so copies of each double strand of DNA multiplies the fluorescence signal by a factor equal to or greater than 100, and the signal to noise ratio is indeed better since the primers and the residual single strands of DNA which cannot be transcribed to RNA do not significantly interfere with the intercalating molecule;

the terminal amplification by transcription permits a better quantification of the PCR procedure carried out upstream. Indeed, this method makes it possible to reduce the number of preliminary PCR cycles and therefore to remain within the purely exponential amplification phase of the type $(1+x)^n$ of the PCR. Futhermore, the additional amplification resulting from the transcription to dsRNA according to the process conforming to the invention is linear; in other words, the amplification factor is constant and does not depend on the quantity of template DNA present in the reaction mixture. An amplification phenomenon which is exponential overall and then linear therefore exists; the analysis of this mathematical function is much simpler than in the case of the conventional PCR technique whose quantification is complicated by the appearance of a plateau beyond the exponential zone.

This better regularity of amplification combined with a simple revealing in one step results in a better accuracy of the measurement, and makes it possible to repeat it easily, thereby facilitating the use of quantitative measurements.

In addition, certain preferred embodiments of the process conforming to the invention permit improvements which are particularly advantageous for the detection of target nucleic acid sequences.

In particular, it is possible, by using the process conforming to the invention, to synthesize RNAs which have a double-stranded structure only on a portion of their length and of which at least one of the ends is in single-stranded form.

These RNAs can be attached to a solid support and/or to a revealing probe via their single-stranded portion.

This permits, in particular, the following applications:

A double-stranded RNA containing one or two single-stranded ends can be produced by simultaneous transcription of two DNA duplexes (each containing a promoter sequence for an RNA polymerase) of which a portion of the sequence is common.

Under these conditions, the RNA obtained is in double-stranded form with one or two single-stranded sequence ends. This RNA hybrid which is obtained with an amplification coefficient greater than 100 can be hybridized to a nucleic acid (recipient nucleic acid) having a sequence complementary to that of one of the ends attached to a solid support.

The recipient nucelic acid (preferably an oligonucleotide) is attached to the support in a covalent or non-covalent manner. Oligonucleotides of differing sequences can be attached to the same support at different locations; thus, several target DNAs can be transcribed in the same bottle, and the transcripts detected on a common support. The revealing is brought about for example by the fluorescence of the double strand of RNA generated by an intercalating compound exposed to UV.

By this means, several target sequences can be treated in the same tube and detected in a specific manner by nucleic acids attached to a support.

The invention will be understood more clearly with the aid of the additional description below, which refers to examples of implementation of the process conforming to the invention.

EXAMPLE 1—Analytical Application Detection of the HPV Virus 6/11 by Fluorescence in Homogeneous Medium After Synthesis of Double-Stranded RNA DNA is detected in a specific manner by a procedure such as that described in PCT application WO 90/15881. The sample is first amplified by a pair of primary primers, this product is then highly diluted and then reamplified by means of primers including in 5' a promoter sequence for T7 RNA polymerase. The transcription to double-stranded RNA is then directly carried out using the amplification product as starting material and the fluorescence of the final product is measured after intercalation of ethidium bromide.

1. Primary PCR

Ten nanograms of DNA from cells, infected or otherwise with papillomavirus type 6/11, are amplified in a volume of 50 µl in the presence of 200 µM of dATP dCTP, dTTP, dGTP, 10 mM of Tris-HCl pH 8.5; 50 mM KCl; 1.5 mM $MgCl_2$; 0.01% gelatin; 2.5 U of Taq polymerase and 10 pmol of oligonucleotide primers.

The position HPV 6/11 and the sequence of the primary primers used are the following

| POSITION | SEQUENCE |
| --- | --- |
| As 1 624-643 | 5'GCTCAGAAGATGAGGTGGAC 3'(SEQ. ID NO:1) |
| As 2 1034-1014 | 5'TTAAACAATGCCTGTGCTTCC 3'(SEQ. ID NO:2) |

25 cycles of three times 1.5 min (92° C., 55° C., 72° C.) are carried out

2. Intermediate 1/200 dilution

2 µl of primary PCR reaction product are diluted in 400 µl of water. 2 µl of this solution are used for the secondary PCR amplification.

3. Secondary PCR

The same reaction medium and the same conditions as for the primary amplification are used; only the composition and the quantity of the secondary primers are changed.

The position in HPV 6/11 and the sequence of the primers carrying in 5' the promoter sequence for T7 RNA pol are the following

| POSITION | SEQUENCE |
| --- | --- |
| a693-713 TG.3'(SEQ. ID NO:3) | 5'TAATACGACTCACTATAGGGTGACCTGTTGCTGTGGATG |
| b 993-975 3'(SEQ. ID NO:4) | 5'TAATACGACTCACTATAGGGGTGTCATCAATAAAGTCC. |

Quantity of primer used : 2 pmol per 50 µl of reaction medium (or 1 pmol per 25 µl).

15 amplification cycles are carried out.

3. Transcription reaction

The transcription to double-stranded RNA is carried out directly on the amplified product; there are added volume for volume, a solution containing 80 mM Tris-HCl, pH 8.0, 50 mM NaCl, 20 mM $MgCl_2$, 4 mM spermidine, 10 mM DTT, 2.5 mM NTP (ribonucleotide triphosphate) and 25 U of T7 RNA polymerase (BRL) in sterile DEPC $H_2O$.

The reaction is carried out at 37° C. for 15 minutes.

4. Fluorescence reading using EtBr

The transcribed product is added to a measurement medium composed of 5 mM Tris-HCl, pH 7.6, 8 mM NaCl, 5 mM EDTA, 0.5 µg/ml EtBr (ethidium bromide).

The conditions for measurement of fluorescence in a Perkin-Elmer spectrofluorimeter are the following: wavelength of excitation 510 nm (sw 8 nm), of emission 590 nm (sw 8 nm), measurement in 1 ml plastic cuvette.

5. Results

Two applied fluorescence techniques in homogeneous medium were compared. The results are illustrated in FIGS. 1 and 2.

FIG. 1: direct measurement of the fluorescence (360/450 nm) of the DNA after PCR amplification, by intercalation of H33 (HOECHST 33258) (0.5 µg/ml)

☐=positive sample, ♦=negative control.

Figure 2:
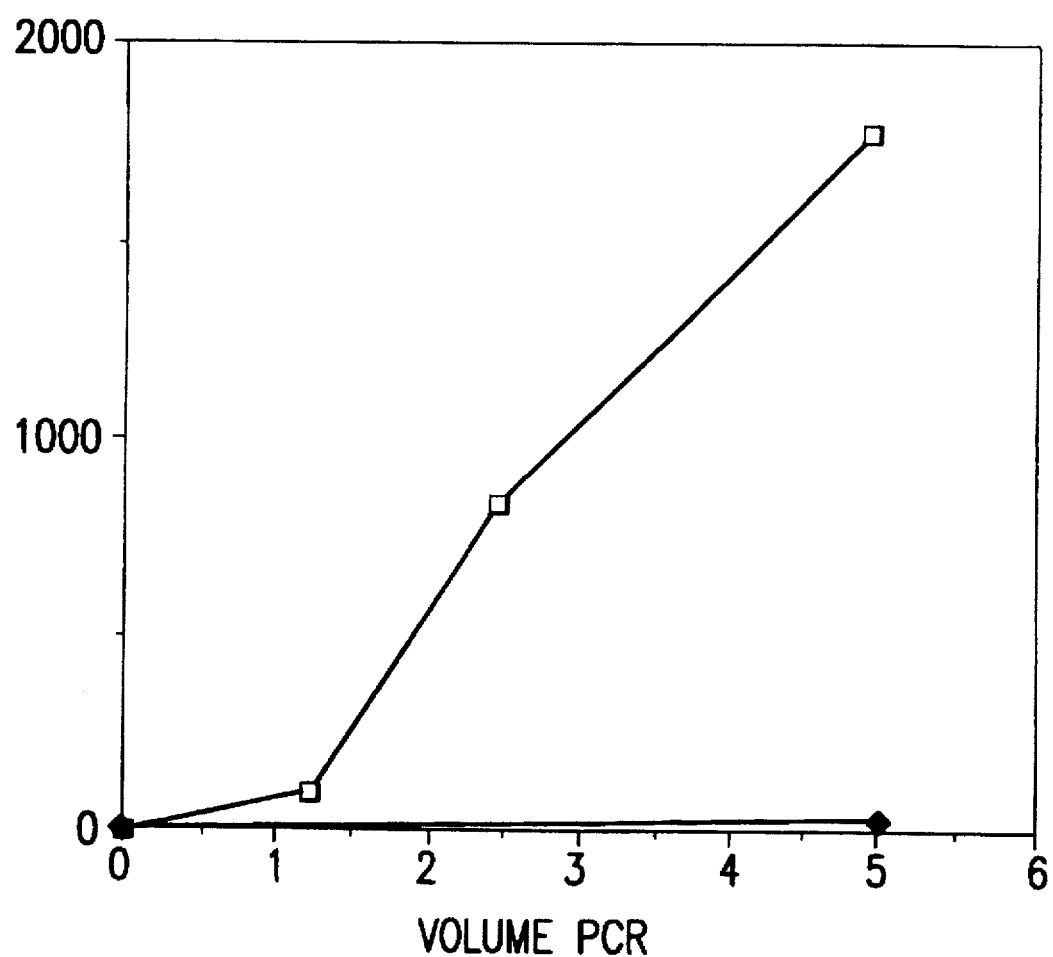
FIG. 2 is a graph depicting the fluorescence of dsRNA synthesized from the DNA using the method of the present invention as described in Example 1.

FIG. 2: measurement with EtBr after transcription to double-stranded RNA according to the method conforming to the invention.

☐=positive sample, ♦=negative control.

The results are expressed, for the same sample of product, by the percentage of fluorescence (in arbitrary units).

Figure 3:
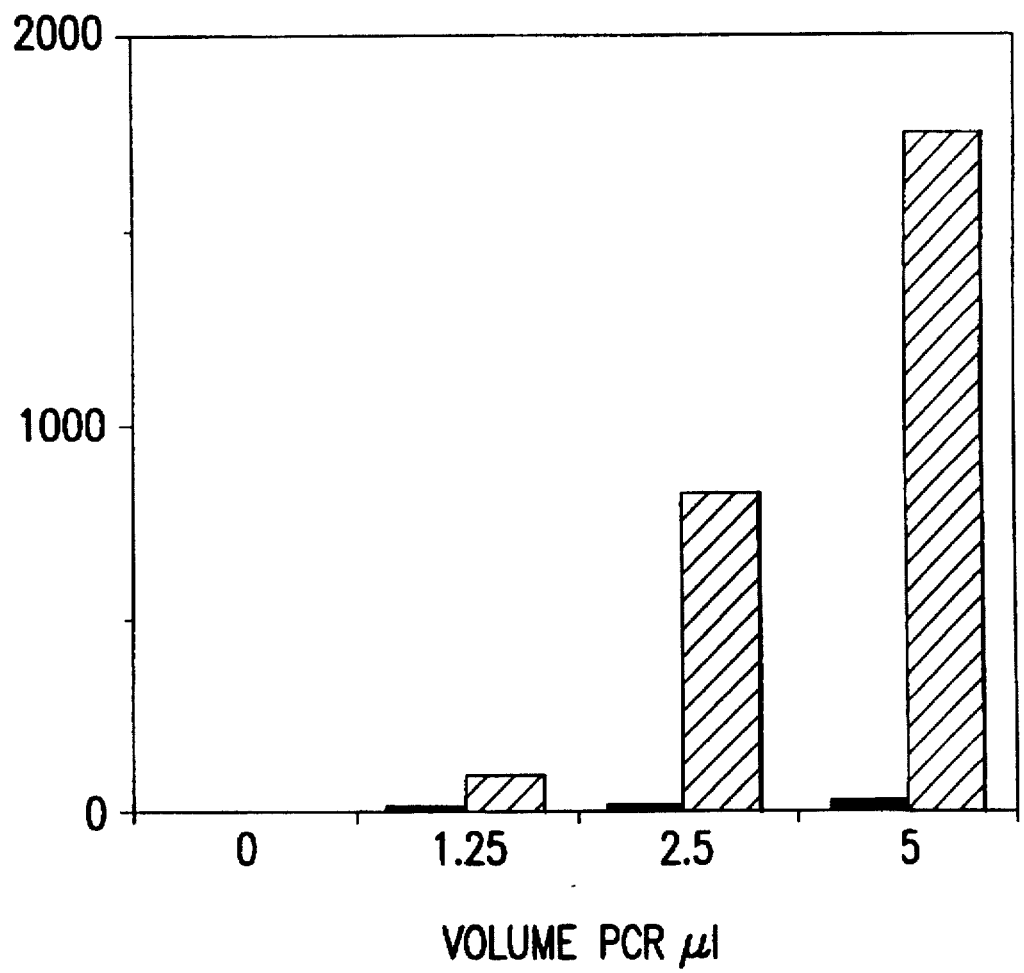
FIG. 3 is a bar graph comparing the DNA after amplification and dsRNA after transcription from the DNA as described in Example 1.

FIG. 3 permits comparison between the intensity of the signals obtained

■ directly after PCR amplification (fluorescence of H33)

☐ after transcription to double-stranded RNA in conformity with the invention (fluorescence of EtBr).

For an equivalent of 5 µl of PCR product, a fluorescence of the DNA of 35 units is measured by H33 (against 5 for the negative) whereas the fluorescence is 1800 units for a similar sample after transcription to a double-stranded RNA and measurement using EtBr (against 12 for the negative).

EXAMPLE 2—Preparative Synthesis of a Double-Stranded RNA by Transcription on a Support A double-stranded DNA template is prepared comprising, on each strand, a promoter for RNA polymerase and a biotin group in 5' of one of the strands. This template is then attached to a support coated with avidin and the transcription is carried out directly on this support.

1. Preparation of the DNA template

The template prepared in this example represents a fragment of the genome of HPV 6/11.

a) Starting with a biological sample

The template is prepared by amplification of a DNA fragment from HPV 6/11. The primary and secondary amplifications are carried out according to the procedure described in Example 1, the T7a primer being previously biotinylated in 5' by the method of ROGET et al; (Nucleic Acids Res., 1989, 17, 7643–7651). If the starting DNA is sufficiently purified, it is possible directly to prepare the template by carrying out a single amplification step in which the T7a primers (biotinylated in 5') and T7b primer are used.

b) Starting with synthetic DNA

The double strand of DNA is produced by partial hybridization of the two oligonucleotides bio-$T_7O_1$ and $T_7O_2$ below, and then extension of the two strands

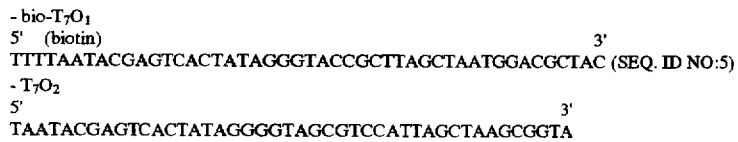

2. Manufacture of the avidin support

A coating of BSA (bovine serum albumin), biotin and then avidin is performed in a Nunc finned tube made from polystyrene (SAUVAIGO et al. Nucl. Acids Res. 1989, 18, 3175–3183). This tube can be preserved for several months at +4° C.

3. Attachment of the DNA template onto the support

Ten microliters of the biotinylated PCR product previously synthesized is attached onto the support by incubation in 100 µl of 0.05M Tris-HCl buffer, pH 9.2, 0.5M NaCl, 2 hours at 37° C. The tube is then rinsed three times with this same buffer in the presence of 0.5% SDS and then once with sterile water.

This support, provided with a DNA template, can be preserved at +4° C. for several weeks.

4. Transcription

The reaction for transcription of the template attached to the support into double-stranded RNA is brought about by 50 U of T7 RNA polymerase (BRL) in 100 µl of 0.04M Tris-HCl, pH 8.0; 8 mM $MgCl_2$; 2 mM spermidine; 25 mM NaCl; 5 mM DTT and 2 mM of ATP, CTP, UTP, GTP.

The reaction is carried out at 37° C. for 30 minutes.

Figure 4:
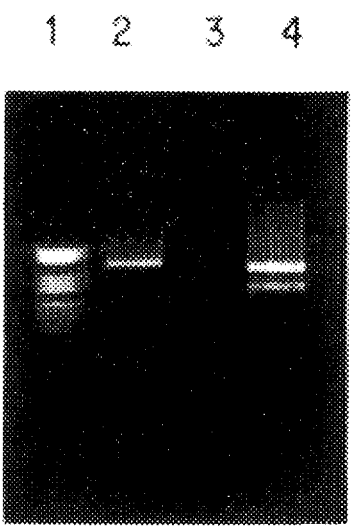
FIG. 4 is an electrophoretic gel showing the integrity of the dsRNA synthesized in Example 2.

5. Isolation and control of the synthesized RNA 100 microliters of reaction medium for transcription are recovered and mixed with 400 µl of cold ethanol. The RNAs are then precipitated at −20° C. and then isolated by centrifugation. The pellet obtained is taken up in sterile water and then quantified by UV spectrometry. The integrity of this double-stranded RNA is controlled by electrophoretic run on agarose gel. The electrophoretic patterns are represented in FIG. 4. The double-stranded structure is demonstrated by a thermal denaturation (heating to 100° C.). The ribonucleotide nature is confirmed by alkaline lysis at high temperature.

About 50 micrograms of RNA (equivalent to 1 (SEQ. ID NO:6) unit of OD at 260 nm) are synthesized during each reaction.

The support, rinsed and stored at +4° C., can be subsequently used several times, without appreciable loss of activity.

EXAMPLE 3—Synthesis of a Double-Stranded RNA Containing a Single-Stranded End of Sequence Specific For the Target DNA: Detection of the HPV6-II Virus The procedure used comprises the formation of 2 duplexes of DNA (each provided with a promoter sequence for T7 RNA polymerase) by 2 PCR reactions carried out in parallel on each sample.

These 2 fractions are combined and then transcribed to RNA which is in a partially double-stranded form.

The RNA obtained contains a double-stranded portion 159 bases long, followed by a single-stranded portion of 141 bases. This product is then hybridized to an oligonucleotide attached onto a nylon membrane and then detected by fluorescence.

1. Formation of the-DNA duplexes

A DNA sample is distributed into 2 tubes. Two PCR amplifications are then independently carried out under the conditions described in Example 1, using the following pairs of primers IT7a                693-713
5'                                                          3'
TAATACGACTCACTATAGGGTGACCTGTTGCTGTGGATGTG    (SEQ. ID NO:3)

Ib'                 852-830
5'                                3'
TGTACCTGAATCGTCCGCCATC    (SEQ. ID NO:7)

IIa                 693-713
5'                           3'
TGACCTGTTGCTGTGGATGTG    (SEQ. ID NO:8)

IT7b                9936-975
5'                                                          3'
TAATACGACTCACTATAGGGGTGTCATCAATAAAGTCC    (SEQ. ID NO:4)

30 cycles (92-55-72, 1, 30) are carried out.

2. Transcription

The two PCR products are mixed volume for volume and 2 volumes of transcription medium containing 25 U of T7 RNA polymerase are added (see Example 1).

The transcription is carried out for 30 minutes at 42° C.

3. Detection of the semi-duplex of RNA on a solid support

An oligonucleotide having a sequence complementary to a portion of the single-stranded end of the RNA is attached to a nylon membrane according to the technique described by SAIKI et al. Proc. Natl. Acad. Sci. USA, 86, 6230–6234 (1989).

Oligonucleotide attached onto the support

HPV6/11 914–940
5'                                          3'
CAGGTACACAAATATCAGACGATGAGG (SEQ. ID NO:9)

The semi-duplex of RNA is hybridized for 1 hour on this support (5×SSPE, 0.1% SOS at 55° C.). The membrane is then rinsed in the same medium for 5 minutes at 55° C. and then rapidly in a 5 mM phosphate buffer, pH 7.0.

The revealing is then carried out by incubation (2 minutes) in a solution at 0.5 µg/ml of ethidium homodimer, in 5 mM phosphate buffer followed by a brief rinsing. The fluorescent spots are then directly observed under radiation at 260 nm and at 520 nm.

The positive samples have a distinct orange-coloured fluorescence whereas the negatives are not distinguishable from the background.

---

We claim:

1. A process for preparing double-stranded RNA comprising the steps of:
 a) providing a DNA comprising a sequence to be transcribed into double-stranded RNA, wherein each strand of said DNA sequence to be transcribed is under transcriptional control of a promoter sequence, and wherein the DNA comprising the DNA sequence to be transcribed is attached to a solid support and;
 b) in a single reaction mixture, contacting said DNA with appropriate RNA polymerase (s) thereby simultaneously transcribing both strands of said DNA sequence and annealing the transcripts to obtain double-stranded RNA.

2. The process of claim 1, wherein the two strands of the DNA sequence to be transcribed are under the transcriptional control of promoter sequences recognized by the same RNA polymerase.

3. The process of claim 1, wherein the two strands of the DNA sequence to be transcribed are under the transcriptional control of promoter sequences recognized by different RNA polymerase.

4. The process of claim 1, wherein the two strands of the DNA sequence to be transcribed belong to two separate DNA molecules.

5. The process of claim 1, wherein the two strands of the DNA sequence to be transcribed are annealed in a single double-stranded DNA molecule.

6. The process of claim 1, which further comprises detecting the presence of double-stranded RNA.

7. A method for detecting the presence of a target nucleic acid sequence in a biological sample, comprising the steps of
 transcribing said target sequence into double-stranded RNA, and
 detecting the presence of said double-stranded RNA;
 wherein if said double-stranded RNA was present, then said target nucleic acid sequence is present in said sample.

8. The method of claim 7 comprising the steps of:
 a) providing a DNA comprising said target sequence obtained from said biological sample, wherein each strand of said target sequence is under transcriptional control of a promoter sequence;
 b) in a single reaction mixture, contacting said DNA with appropriate RNA polymerase(s) thereby simultaneously transcribing both strands of said target sequence and immediately annealing the transcripts to obtain double-stranded RNA
 c) detecting the presence of said double-stranded RNA.

9. The method of claim 8, wherein said DNA comprising said target sequence is obtained from said biological sample by an amplification process such as polymerase chain reaction.

10. The method of claim 8, wherein the product of transcription of the DNA comprising the target sequence comprises a segment of single-stranded RNA, and wherein said transcription product is attached onto a solid support via said single-stranded RNA segment.

11. The method of claim 8, wherein several different target sequences are transcribed and detected simultaneously in the same sample.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
    ( A ) LENGTH: 20 base pairs
    ( B ) TYPE: nucleic acid
    ( C ) STRANDEDNESS: unknown
    ( D ) TOPOLOGY: unknown ( i i ) MOLECULE TYPE: Other nucleic acid ( x i ) SEQUENCE DESCRIPTION: SEQ ID NO:1:

GCTCAGAAGA TGAGGTGGAC                                         20

( 2 ) INFORMATION FOR SEQ ID NO:2:

( i ) SEQUENCE CHARACTERISTICS:
    ( A ) LENGTH: 21 base pairs
    ( B ) TYPE: nucleic acid
    ( C ) STRANDEDNESS: unknown
    ( D ) TOPOLOGY: unknown ( i i ) MOLECULE TYPE: Other nucleic acid ( x i ) SEQUENCE DESCRIPTION: SEQ ID NO:2:

TTAAACAATG CCTGTGCTTC C                                       21

( 2 ) INFORMATION FOR SEQ ID NO:3:

( i ) SEQUENCE CHARACTERISTICS:
   ( A ) LENGTH: 41 base pairs
   ( B ) TYPE: nucleic acid
   ( C ) STRANDEDNESS: unknown
   ( D ) TOPOLOGY: unknown ( i i ) MOLECULE TYPE: Other nucleic acid ( x i ) SEQUENCE DESCRIPTION: SEQ ID NO:3:

TAATACGACT CACTATAGGG TGACCTGTTG CTGTGGATGT G    41

( 2 ) INFORMATION FOR SEQ ID NO:4:

( i ) SEQUENCE CHARACTERISTICS:
      ( A ) LENGTH: 38 base pairs
      ( B ) TYPE: nucleic acid
      ( C ) STRANDEDNESS: unknown
      ( D ) TOPOLOGY: unknown ( i i ) MOLECULE TYPE: Other nucleic acid ( x i ) SEQUENCE DESCRIPTION: SEQ ID NO:4:

TAATACGACT CACTATAGGG GTGTCATCAA TAAAGTCC    38

( 2 ) INFORMATION FOR SEQ ID NO:5:

( i ) SEQUENCE CHARACTERISTICS:
      ( A ) LENGTH: 47 base pairs
      ( B ) TYPE: nucleic acid
      ( C ) STRANDEDNESS: unknown
      ( D ) TOPOLOGY: unknown ( i i ) MOLECULE TYPE: Other nucleic acid ( x i ) SEQUENCE DESCRIPTION: SEQ ID NO:5:

TTTTAATACG AGTCACTATA GGGTACCGCT TAGCTAATGG ACGCTAC    47

( 2 ) INFORMATION FOR SEQ ID NO:6:

( i ) SEQUENCE CHARACTERISTICS:
      ( A ) LENGTH: 44 base pairs
      ( B ) TYPE: nucleic acid
      ( C ) STRANDEDNESS: unknown
      ( D ) TOPOLOGY: unknown ( i i ) MOLECULE TYPE: Other nucleic acid ( x i ) SEQUENCE DESCRIPTION: SEQ ID NO:6:

TAATACGAGT CACTATAGGG GTAGCGTCCA TTAGCTAAGC GGTA    44

( 2 ) INFORMATION FOR SEQ ID NO:7:

( i ) SEQUENCE CHARACTERISTICS:
      ( A ) LENGTH: 22 base pairs
      ( B ) TYPE: nucleic acid
      ( C ) STRANDEDNESS: unknown
      ( D ) TOPOLOGY: unknown ( i i ) MOLECULE TYPE: Other nucleic acid ( x i ) SEQUENCE DESCRIPTION: SEQ ID NO:7:

TGTACCTGAA TCGTCCGCCA TC    22

( 2 ) INFORMATION FOR SEQ ID NO:8:

( i ) SEQUENCE CHARACTERISTICS:
      ( A ) LENGTH: 21 base pairs
      ( B ) TYPE: nucleic acid
      ( C ) STRANDEDNESS: unknown (D) TOPOLOGY: unknown (i i) MOLECULE TYPE: Other nucleic acid (x i) SEQUENCE DESCRIPTION: SEQ ID NO:8:

TGACCTGTTG CTGTGGATGT G    21

(2) INFORMATION FOR SEQ ID NO:9:

(i) SEQUENCE CHARACTERISTICS:
      (A) LENGTH: 27 base pairs
      (B) TYPE: nucleic acid
      (C) STRANDEDNESS: unknown
      (D) TOPOLOGY: unknown (i i) MOLECULE TYPE: Other nucleic acid (x i) SEQUENCE DESCRIPTION: SEQ ID NO:9:

CAGGTACACA AATATCAGAC GATGAGG    27